United States Patent
Araki et al.

(10) Patent No.: US 6,572,530 B1
(45) Date of Patent: Jun. 3, 2003

(54) BLOOD CIRCULATION AUXILIARY DEVICE USING CONTINUOUS BLOOD FLOW PUMP AND DIAGNOSIS DEVICE FOR BLOOD CIRCULATION STATE IN ORGANISM

(75) Inventors: Kenji Araki, Miyazaki (JP); Mitsuo Oshikawa, Miyazaki (JP); Hirohumi Anai, Ooita (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 09/582,465

(22) PCT Filed: Dec. 24, 1998

(86) PCT No.: PCT/JP98/05928

§ 371 (c)(1),
(2), (4) Date: Jun. 26, 2000

(87) PCT Pub. No.: WO99/33502

PCT Pub. Date: Jul. 8, 1999

(30) Foreign Application Priority Data

Dec. 27, 1997 (JP) .............................. 9-367523

(51) Int. Cl.⁷ .............................................. A61N 1/362
(52) U.S. Cl. ....................................................... 600/17
(58) Field of Search ..................... 606/16–18; 604/6.11, 604/4.01

(56) References Cited

U.S. PATENT DOCUMENTS 5,385,581 A 1/1995 Bramm et al.
6,129,660 A 10/2000 Nakazeki et al.
6,293,901 B1 * 9/2001 Prem

FOREIGN PATENT DOCUMENTS

| DE | 196 34 180 A1 | 2/1997 |
| JP | 8-238310 | 9/1996 |
| JP | 9-56812 | 3/1997 |

* cited by examiner

Primary Examiner—Mark Bockelman
(74) Attorney, Agent, or Firm—Merchant & Gould P.C.

(57) ABSTRACT

A blood circulation assisting device using a continuous flow blood pump (1) for blood feeding assistance to remove blood through a blood removing pipe (2) and drive out blood at a predetermined flow rate through a blood feeding pipe (3). The blood circulation assisting device includes a current measuring unit (7) for measuring current flowing through a motor (4) driving the pump (1) in order to use the current as data corresponding to a blood flow rate through the continuous flow blood pump (1) and an amplitude detection unit (8) for detecting, from an output of the current measuring unit (7), the amplitude of fluctuation of current flowing through the motor (4) in order to use the amplitude as data corresponding to a flow rate amplitude due to flow rate fluctuation. The amplitude of this fluctuation is divided by an average current value and output as an amplitude index. By controlling the speed of the motor (4) so that the amplitude index, which is the output of the amplitude detection unit (8), is within a predetermined value, a blood feeding assistance is kept in an optimum state matching a blood circulation state in an organism.

22 Claims, 6 Drawing Sheets

BLOOD CIRCULATION AUXILIARY DEVICE USING CONTINUOUS BLOOD FLOW PUMP AND DIAGNOSIS DEVICE FOR BLOOD CIRCULATION STATE IN ORGANISM

This application is a 371 of PCT/JP98/05928

TECHNICAL FIELD

The present invention relates to a blood circulation assisting device using a continuous flow blood pump for blood feeding assistance and a diagnosis device for evaluating blood circulation state in an organism using the same.

BACKGROUND ART

Pulsatile blood flow pumps for use in blood circulation assistance include positive-displacement pumps such as a diaphram type and a pusher plate type. The ejection of the positive-displacement pump is controlled so as to satisfy the needs of an organism by being driven with a complete-filling complete-ejection mode. However, the positive-displacement pumps face difficulty in the development as an artificial heart because their structure is complicated.

On the other hand, continuous flow blood pumps have been developed for the purpose of assisting blood circulation in organism. They include not only typical types such as a centrifugal pump, an axial flow pump and a mixed flow pump, but ones which drive out blood by using a rotor, a precessional moving body, a swaying moving body, oscillations or undulations. Since their structure is simple and they can be manufactured at low cost, they show greater promise than the positive-displacement pumps. However, it is said that the continuous flow blood pumps are more difficult to control than the positive-displacement pumps.

In order to perform the circulation assistance satisfying the needs of organism, a method for monitoring one or the combination of blood pressure, blood flow rate of a pump or an organism, sympathetic nerve activity and venous oxygen saturation by using a specific sensor has been invented. However, sensors that can endure a continuous use for a long period of time without a replacement have not been developed.

In order to eliminate the use of any specific sensor, the following method for controlling the drive of the continuous flow blood pump has been proposed. The method employs a mean motor current consumption and a hydraulic performance of the pump in use to estimate the pump flow rate, thereby maintaining a constant flow rate. In other words, in the continuous flow blood pump, the correlation can be obtained between a pump speed, a generated pressure head (pressure), a pump flow rate and a motor current consumption. Therefore, when the pump speed and the motor current consumption are known, the generated pressure head and flow rate of the pump can be estimated. In addition, the pump speed and the motor current consumption can be taken and used as internal data of the motor without using any specific sensor. As a result, the pump speed can be controlled with a simple structure so as to maintain the constant flow rate. (Cf., "Control of Centrifugal Blood Pump Based on the Motor Current", Tatsuhiko Iijima, et. al., Artificial Organs Vol. 21, No. 7, 1997, Japanese Society of Artificial Organs.)

However, the controlling method in which the pump flow rate is estimated by a mean motor current consumption and a hydraulic performance of the pump in use, thereby maintaining a constant flow rate, has several problems.

Firstly, the controlling method cannot perform an appropriate blood circulation assistance in an organism. The blood flow rate needed by an organism varies very much according to the individual's condition. For example, size, state of activity and circulated blood volume of the individual have influence on the optimal blood flow rate. Specifically, the usual cardiac output of an infant having a body weight of 10 kg is approximately 1 L/min, while the cardiac output of an adult during exertion may exceed 10 L/min. Therefore, the controlling method of merely maintaining the constant pump flow rate is not suitable for the appropriate blood circulation assistance in an organism.

Secondly, since the motor current consumption is influenced by a kinematic viscosity of the liquid during feeding, when the liquid is blood, for example, its change in character causes a large error in estimating the pump flow rate. What influences the kinematic viscosity of blood are factors such as the number of red cell (or hematocrit value), serum lipids value or serum whole protein value. These values fluctuate according to the physiological state of an organism. However, there is no method developed for continuously monitoring the kinematic viscosity or component concentration of blood. Thus, it is difficult to achieve a method for controlling a blood feeding so as to obtain the desired flow rate free from the influence by the blood characteristic such as the kinematic viscosity.

It is an object of the present invention to solve the problems of the prior art mentioned above and to provide a blood circulation assisting device using a continuous flow blood pump that realizes an appropriate circulation assistance matching a blood circulation state in an organism as well as the desired flow rate without using any specific sensor for monitoring blood character.

DISCLOSURE OF INVENTION

The blood circulation assisting device according to the present invention includes a continuous flow blood pump made of a non-displacement-type pump for blood feeding assistance, a blood removing pipe having one end attachable to a blood removal site in an organism and the other end connected to an inflow portion of the continuous flow blood pump, a blood feeding pipe having one end attachable to a blood feed site in the organism and the other end connected to an outflow portion of the continuous flow blood pump. Blood is removed via the blood removing pipe and driven out via the blood feeding pipe by the continuous flow blood pump so as to attain a predetermined flow rate. The blood circulation assisting device further includes a flow rate detection means for directly or indirectly obtaining data corresponding to a blood flow rate flowing through the continuous flow blood pump, a flow rate amplitude detection means for obtaining, from an output of the flow rate detection means, data corresponding to a fluctuation amplitude of the flow rate, and a means for adjusting an output of the flow rate amplitude detection means to a predetermined value.

With the above configuration, the flow rate amplitude detection means provides an output according to the blood circulation state in an organism, so circulation assistance matching the blood circulation state in the organism can be achieved easily by the control based on the output. In order to show more clearly that the device with the above configuration can achieve the object of the present invention, clinical backgrounds regarding blood circulation assistance and more detailed effects of the device with the above configuration are explained in the following.

Pulsation of Consumption Current Waveform of Continuous Flow Blood Pump

When a continuous flow blood pump is under usual operation, it drives out a continuous flow, and its consumption current does not show pulsation. On the other hand, unless the heart of an organism is under cardiac arrest or an arrhythmic state close to the cardiac arrest, it generates a pulsatile flow. Accordingly, when the continuous flow blood pump is used for circulation assistance in an organism, a pump flow that initially is a continuous flow is influenced by a pulsation of native cardiac output, and begins to show pulsation. As a result, current waveform of the motor, which drives the pump, also shows pulsation.

We noted this specific pulsation appeared when used in an organism, and found that an appropriate circulation assistance was made possible by referring to a pulsation of consumption current value rather than to a mean value of motor current consumption.

Relationship Between Motor Speed and Consumption Current Waveform

In the following, with respect to blood circulation assistance, "total assistance" refers to the case where cardiac output of an organism is not seen, and the blood pump drives out all the blood. However, this does not necessarily mean cardiac arrest, so the heart of the organism may generate some pressure. On the other hand, "partial assistance" refers to the state where the cardiac output of an organism is apparent, and at the same time the blood pump also drives out blood.

① t-point

When the pump speed is low, native cardiac out put surpasses pump output, and blood circulates in an organism with pulsatile flow. Therefore, the consumption current waveform of the motor also shows pulsation. As the pump speed becomes higher, the pump output comes close to the native cardiac output, and then comes to the same level. This point is called t-point (originating from a term "total assist point") in the present invention. When the pump speed is further raised above the t-point, pump output exceeds native cardiac output and the native cardiac output disappears, which means that the assist condition changes from partial to total assistance. Thus, the circulation in the organism changes from pulsatile to continuous flow. Consequently, the pulsation of the motor current waveform decreases gradually.

This is shown in the graph of FIG. 1. This graph illustrates an example of a relationship between the motor speed and each monitoring indicator. Since this graph will be explained in detail later, only an index of current amplitude is described here. The index of current amplitude is a value obtained by dividing the amplitude of current fluctuation with simultaneous mean current value. The reason the index of current amplitude is used is as follows.

The mean value of motor current consumption increases along with the speed increase. Therefore, current consumption amplitude also tends to increase along with the speed increase, even if the condition of an organism does not change. Consequently, it is difficult directly to detect the alteration of pulsatile flow of the circulation in the organism from the alteration of amplitude of current fluctuation. In other words, the absolute value of the amplitude of current fluctuation is influenced by the motor speed change. In order to detect only the alteration of pulsatile flow of the circulation in the organism, it is desirable that the index of current amplitude is used as an indicator. As is described in the following, when the alteration of pulsatile flow is detected with a flow meter, which directly measures blood flow rate rather than motor current, such an indicator is unnecessary in essence.

The t-p point and t-i point correspond to t-point mentioned above. The points at which the assist condition of the pump turns from partial to total assistance are distinguished based on an identification technique. Thus, the point that is identified by systolic aortic pressure and systolic left ventricular pressure is termed the t-p point, and the point that is identified by the index of current amplitude is termed the t-i point. As is described below, these two points substantially match. The t-point in this section refers to the t-i point.

As is clearly shown in FIG. 1, the t-point is a specific point that clearly appears as the motor speed increases.

② s-point

As pump speed increases, a sucking phenomenon starts occurring at the blood removal site. In general, the sucking occurs intermittently, corresponding to pulsation of the heart in an organism, and causing pulsation in blood flow in the pump. In the case of appropriate blood removal by the pump and not being short of blood volume, the sucking becomes apparent at the pump speed higher than the t-point, that is still higher than the speed when the circulation in the organism and the pump come extremely close to the continuous flow. Thus, the amplitude of the fluctuation of consumption current waveform becomes the smallest when coming close to a continuous flow, and becomes larger again when the sucking becomes distinct. This point is called s-point (originating from a "sucking point") in the present invention. As is shown in FIG. 1, the index of current amplitude becomes larger beyond the s-point.

As is described above, when the relationship between motor speed and current fluctuation amplitude is shown with motor speed and the index of current amplitude (a value obtained by dividing the amplitude with mean current value), there are two specific points, that is, the t-point at which the circulation assistance changes from partial to total assistance and the s-point at which the pulsation of blood flow in the pump starts occurring due to sucking.

Meaning of Specific Points t and s, and Application Thereof to Diagnosis of the Circulation State in an Organism and to Pump Control As is mentioned above, the t-point is the point at which the circulation assistance by the pump changes from partial to total assistance. In order to make this total assistance possible, it is necessary that the pump can generate a pressure head sufficient to drive out the entire venous return volume and maintain flow rate. The pressure head is a pressure difference between inlet and outlet tubes of the pump and heavily depends on the blood pressure of the feeding side in an organism. Since this blood pressure is defined by the venous return volume and peripheral vascular resistance in an organism, the t-point also depends mainly on the venous return volume and peripheral vascular resistance.

Now, assuming that a circulation state in an organism has changed, thus changing the pump speed corresponding to the t-point, the speed increase indicates an increase of the venous return when the blood pressure is unchanged. On the other hand, it indicates an increase of the blood pressure when the venous return is unchanged. The speed decrease indicates vice versa. In other words, since the t-point changes according to the circulation state in an organism, controlling pump speed so as to always exist at the t-point or near the t-point provides circulation assistance that is neither too much nor too little for an organism according to the change in the organism.

Near the t-point means the range that provides practically sufficient accuracy to estimate the change of circulation state in an organism. For example, it is the speed within the range of ±2 to 3% of the speed at the t-point.

Controlling the pump speed based on the t-point is an example showing the possibility of the control corresponding to the circulation state in an organism with using the amplitude of flow rate fluctuation such as the amplitude of the motor current consumption fluctuation mentioned here. Therefore, a control base can be selected according to the specific purpose.

In the above description, only the circulation assistance is mentioned. Further it is possible to apply the fluctuation amplitude of consumption current waveform at the t-point or near the t-point to diagnosis of inflow state at a blood inflow portion and filling state in the heart.

The s-point is the point at which the pulsation of blood flow in the pump becomes apparent due to sucking. When the blood inflow portion of the blood removing pipe in the pump has no problem and sucking is unlikely to occur, the amplitude of current value fluctuation is substantially zero at the s-point or near the s-point, reflecting that a continuous flow has been generated in the pump. Therefore, the current amplitude at the s-point can be used for detecting a problem in the blood inflow portion of the blood removing pipe in the pump, such as blood removal failure due to improper location of the blood removing pipe, formation of a thrombosis or other obstructions, or distinctive decrease of blood volume (dehydration or shock), thus controlling blood circulation assistance appropriately. The amplitude of current value fluctuation near the s-point, even if it is not exactly the s-point, provides the control satisfactory enough in an actual use. Near the s-point means the range that provides practically sufficient accuracy to estimate the change of circulation state in an organism. For example, it is the speed within the range of ±2 to 3% of the speed at the s-point. In addition, "substantially zero" described above means the range of current amplitude that can be used for detecting the problems at the s-point or near the s-point and realize an appropriate control of blood circulation assistance.

Also, the s-point or near the s-point is the point at which distinctive sucking does not occur and the heart of an organism generates the lowest pressure. This means that the maximum effect of stress reduction of the heart can be obtained safely. Thus, controlling the pump speed so as to always exist at the s-point or near the s-point realizes the safe and maximum effect of stress reduction of the heart.

As it is clear with the above description, controlling the pump speed so as always to be substantially between the t-point and the s-point realizes the safe and effective circulation assistance, which is neither too much nor too little for an organism and provides the maximum effect of stress reduction of the heart.

Indicator for Control

Any indicators directed to the measurement parameter, which is influenced by a pulsation of an organism and is reflected on the continuous flow blood pump, can be used in controlling the pump device. In particular, the present invention uses a pulsation amplitude as this indicator for control. Also, when using the current value of a pumping motor, the indicator for control may be a numerical value that is made into an indicator based on a pulsation amplitude of the current value. Specifically, they may be such a value as the one obtained by dividing the amplitude of the current value fluctuation of a pumping motor with a mean current value or the one obtained by dividing the amplitude with a current consumption difference between open operation period and closed operation period at the same pump speed (theoretical maximum amplitude). "Open operation period" is the case where a pump is operated with the conduit, which is communicated with the outflow portion of the pump, being open. On the contrary, "closed operation period" is the case where a pump is operated with the conduit being closed.

Sensor

The present invention does not require the specific sensor such as the one for monitoring a blood character. Mere flow rate measurement can detect blood circulation. The flow rate measurement may be conducted directly with a flow rate sensor or indirectly with other measuring means.

As the indirect measuring means, for example, motor consumption current of a continuous flow blood pump can be used. Consumption current multiplied by voltage makes electric power, so the electric power may also be used. Since consumption current can be obtained as an internal data of a motor, a sensor is not needed, leading to simplification of the device, improvement of reliability and safety, increase of long-term durability, cost reduction, miniaturization, etc.

A direct means of measuring flow rate is a flow rate sensor such as an ultrasonic flow meter. Since it is conventionally used as a sensor, the structure of the device is far simpler than in the case where a specific sensor for monitoring blood characteristics is needed.

Pump Type, Location of the Pump and Assisting Period by the Pump

The pump used in the present invention may be any continuous flow blood pump and is not limited to a specific pump. The pump may be located either externally or internally, and the assisting period may be either short or long. A blood removal site and a blood feed site are not limited. Assistance may be either in the right ventricle or left ventricle.

As is clearly shown in above description, the present invention may be embodied in various modes in the following that are suitable for actual use, in addition to above basic configurations.

An output corresponding to the flow rate may be obtained by using means for measuring a current consumption or a power consumption value of the motor for the continuous flow blood pump, whereby the flow rate detection means is configured. Alternatively, an output corresponding to the flow rate is obtained by using a flow sensor, disposed near the continuous flow blood pump, whereby the flow rate detection means is configured. In this manner, a simple device can be configured without any specific sensor for monitoring blood characteristics.

Moreover, the flow rate amplitude detection means may be configured so that it detects a maximum value and a minimum value of the output of the flow rate detection means at predetermined time intervals and outputs the maximum and the minimum value. Alternatively, the flow rate amplitude detection means is configured so that it detects a maximum value and a minimum value of the output of the flow rate detection means at predetermined time intervals and outputs a flow rate amplitude that is a difference between the maximum and the minimum values. Alternatively, the flow rate amplitude detection means is configured so that it detects a mean value and a fluctuation amplitude of output of the flow rate detection means at predetermined time intervals and outputs an amplitude index that is obtained by dividing the amplitude with the mean output. In this manner, the desired output according to a control method can be obtained.

Furthermore, the blood circulation assisting device may be configured so that it includes a display means for displaying the output of the flow rate amplitude detection means and a means for manually operating and adjusting a speed of the motor, thereby providing a simple device that easily can perform appropriate blood circulation assistance.

The blood circulation assisting device further may include a means for controlling a speed of the motor for driving the pump according to the output of the flow rate amplitude detection means so that the flow rate amplitude is within a predetermined range. Alternatively, it further includes a means for controlling a speed of the motor for driving the pump according to the output of the flow rate amplitude detection means so that the flow rate amplitude index is within a predetermined range. The above configurations provide a device that performs an automatic control for appropriate blood circulation assistance.

Furthermore, in the above-described device including the means for controlling a speed of the motor according to the output of the flow rate amplitude detection means so that the flow rate amplitude is within the predetermined range, the controlling means may be configured as follows. With the device being attached to an organism, the motor speed of the continuous flow blood pump is changed, so that the t-point at which circulation assistance by the pump changes from partial to total assistance is detected based on an output change of the flow rate amplitude detection means caused by the change of the motor speed. The motor speed is controlled so as to be in a predetermined relationship to the motor speed at the detected t-point. Alternatively, the motor is controlled so as to have a speed at the t-point or near the t-point. In this manner, an optimal operation is realized according to a clinical condition of an organism.

Furthermore, in the above-described device including the means for controlling a speed of the motor according to the output of the flow rate amplitude detection means so that the flow rate amplitude is within the predetermined range, the controlling means may be configured as follows. With the device being attached to an organism, the motor speed is changed, so that the s-point, at which a fluctuation of the flow rate amplitude becomes distinctive because a blood inflow port of the blood removing pipe starts sucking on to a wall of the organism, is detected based on an output change of the flow rate amplitude detection means caused by the change of the motor speed. The motor speed is controlled so as to be in a predetermined relationship to the motor speed at the detected s-point. Alternatively, the s-point is detected similarly based on the flow rate amplitude index, and the motor speed is controlled so as to be in a predetermined relation to the motor speed at the detected s-point. Alternatively, the motor is controlled so as to have a speed corresponding to the speed between near the t-point and near the s-point. Alternatively, a blood circulation is assisted so that the flow rate amplitude at the s-point is as small as possible and substantially zero. Alternatively, the motor speed is controlled so that when the motor speed is changed within a predetermined range, a correlation between the motor speed and index of current amplitude is negative. Above configurations realize a device that provides the safe and maximum stress reduction effect of the heart.

A diagnosis apparatus for blood circulation state includes the blood circulation assisting device described above, and is configured as follows: with the device being attached to an organism, the motor speed of the continuous flow blood pump is changed, so that the t-point at which circulation assistance by the pump changes from partial to total assistance is detected based on an output change of the flow rate amplitude detection means caused by the change of the motor speed. An inflow state at a blood inflow port and/or filling state of a heart are detected based on the flow rate amplitude at the detected t-point or near the t-point. Alternatively, the t-point is detected in a similar manner, so that the change of the motor speed at the detected t-point or near the t-point is detected, and a change of circulation state in the organism is detected with the speed change. Alternatively, in a similar manner, when the motor speed at the t-point or near the t-point increases, unchanged blood pressure is judged as an increase of venous return or unchanged venous return is judged as an increase of blood pressure. On the other hand, when the motor speed at the t-point or near the t-point decreases, unchanged blood pressure is judged as a decrease of venous return or unchanged venous return is judged as a decrease of blood pressure. Above configurations provide a diagnosis apparatus that can easily diagnose blood circulation state in an organism with a simple structure.

Furthermore, the apparatus may be configured by using the above-described blood circulation assisting device, so that the s-point is detected as mentioned above, and an inflow state at the blood inflow port and/or filling state of a heart are detected based on the flow rate amplitude at the detected s-point or near the s-point. Alternatively, the s-point is detected in a similar manner, the speed at the detected s-point or near the s-point is detected, and a change of circulation state in the organism is diagnosed with the speed change. Above configurations realize a diagnosis device for preventing an injury due to sucking from generating.

A blood circulation assisting method in which the blood circulation assisting device with above configuration is attached to the organism to assist blood circulation can easily realize appropriate circulation assistance for a blood circulation state in the organism.

A method for diagnosing an organism in which the diagnosis device with the above configuration is attached to the organism to diagnose a blood circulation state easily can diagnose a blood circulation state in the organism.

BEST MODE FOR CARRYING OUT THE INVENTION

Figure 2A:
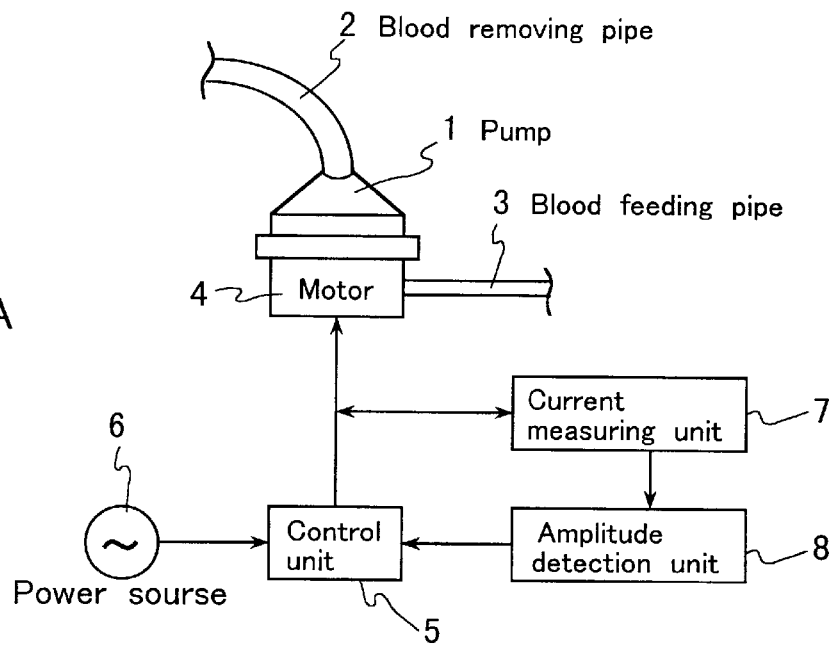
FIG. 2A is a block diagram showing a blood circulation assisting device in accordance with one embodiment of the present invention.

The following is a description of the preferred embodiments of a blood circulation assisting device according to the present invention, with reference to FIG. 2A.

Numeral 1 denotes a continuous flow blood pump, which may be of various types such as a centrifugal pump, an axial flow pump, a mixed flow pump and pumps that drive out blood by using a rotor, a precessional moving body, a swaying moving body or oscillations and undulations. A blood removing pipe 2 is connected to the inlet port of the pump 1, and a blood feeding pipe 3 is connected to the outlet port. When using the device, a free end of the blood removing pipe 2 is attached to a blood removal site in an organism, and a free end of the blood feeding pipe 3 is attached to a blood feeding site. A motor 4 drives the pump 1.

The motor 4 is connected to a power source 6 via a control unit 5. A current measuring unit 7 is connected so as to measure current consumption of the motor 4. An output of the current measuring unit 7 is applied to an amplitude detection unit 8. The amplitude detection unit 8 detects the amplitude of current value fluctuation from the output of the current measuring unit 7 and outputs the result to the control unit 5. The control unit 5 controls the speed of the motor 4 based on the output of the amplitude detection unit 8.

The current measuring unit 7 extracts current waveform at a sample rate of 120 Hz for 3 seconds, for example, and outputs data processed with A/D conversion. The amplitude detection unit 8 calculates maximum and minimum values of the data and difference thereof to detect the amplitude of current fluctuation.

The current value of the motor 4 detected by the current measuring unit 7 corresponds to a flow rate of the pump 1. Thus, an index of current amplitude, which is an output of the amplitude detection unit 8, corresponds to amplitude of a flow rate. In other words, the current measuring unit 7 forms flow rate detection means and the amplitude detection unit 8 forms flow rate amplitude detection means.

For the reason described in the section of "<Relationship between motor speed and consumption current waveform>" in "Disclosure of the Invention", it is desired that the amplitude detection unit 8 outputs an index of current amplitude that is obtained by dividing the amplitude of current fluctuation with simultaneous mean current value, rather than the amplitude of current fluctuation itself.

It is necessary that, in order at least to detect the amplitude of flow rate fluctuation due to intervals of native cardiac pulsation, the current measuring unit 7 is properly set at the time for measuring the amplitude.

The following is an example of the control performed by the control unit 5.

The control unit 5 changes speed of the motor 4 and identifies the t-point or the s-point by using the index of current amplitude, which is an output of the amplitude detection unit 8. The motor may be controlled based on the speed corresponding to the identified t-point or s-point. For example, the motor is controlled so as to maintain the speed near the t-point.

Figure 1:
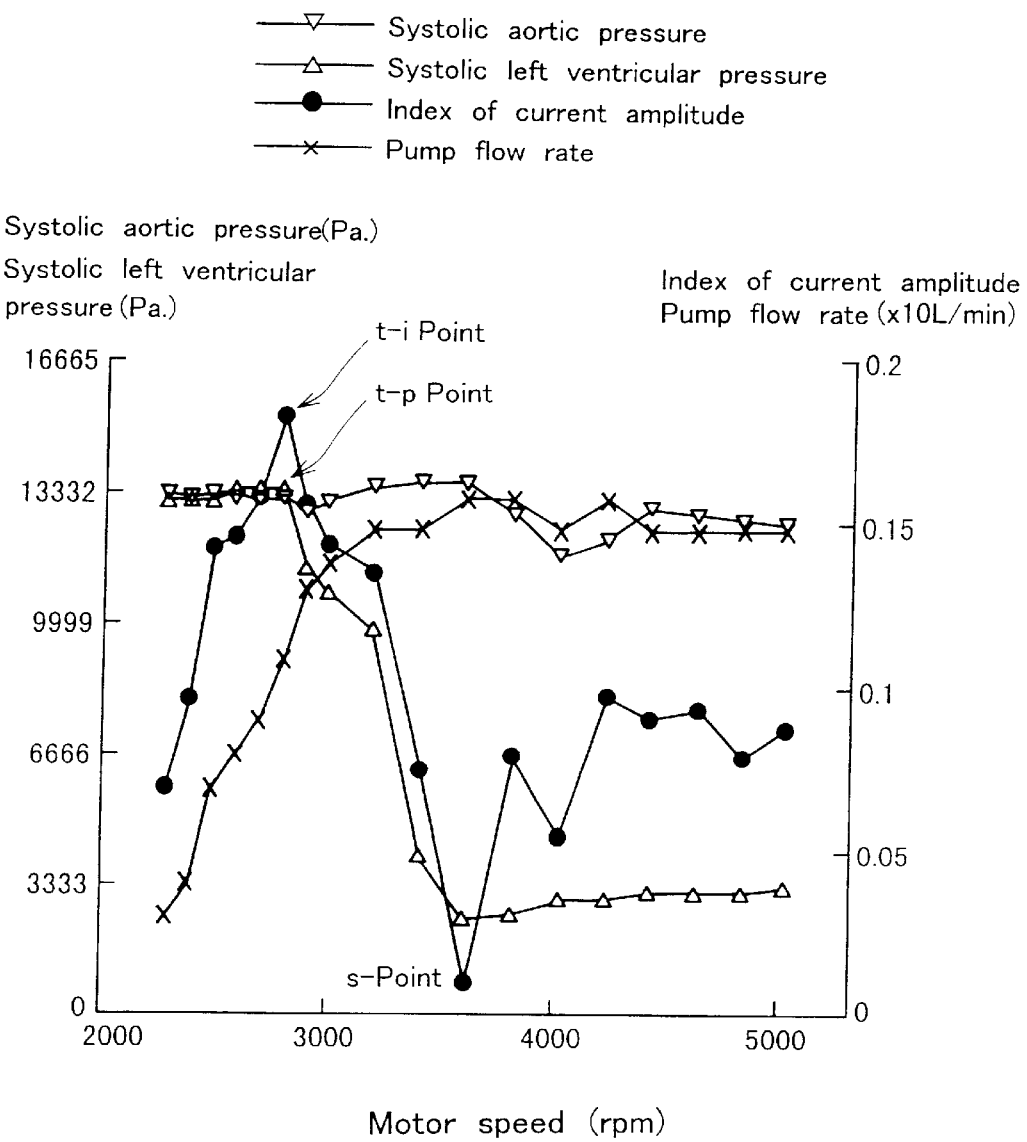
FIG. 1 is a graph showing an example of the relationship between speed of a motor for driving a pump and each monitoring indicator.

The t-point or s-point is identified based on the characteristics indicated in the graph shown in FIG. 1. As is shown in this figure, the index of current amplitude shows a stable decrease between the t-point and the s-point. In other words, the motor speed and the index of current amplitude show a negative correlation. Therefore, it is possible to detect whether the speed of the motor 4 is within the speed range corresponding to that between the t-point and the s-point by-forcing the speed of the motor 4 to change at constant time intervals in a sufficiently wide speed range, and then detecting whether the correlation above is positive or negative. A sufficiently wide speed range means that it is sufficient to eliminate a temporary fluctuation of the index of current amplitude, such as the fluctuation appearing at the speed higher than the s-point shown in FIG. 1, and proper range may be selected clinically. In this manner, the speed range where the motor speed and the index of current amplitude show negative correlation is detected, and the starting point thereof is identified the t-point. Similarly, the end point of the speed range is detected and identified the s-point. Such processes can be carried out easily by a computer if the output of the amplitude detection unit 8 is digitized as is described above.

The above knowledge that when the speed of the motor 4 is between the t-point and the s-point, the motor speed and the index of current amplitude show negative correlation can be used effectively for the control. In other words, the speed of the motor 4 is forced to change for a certain period of time, the state of correlation mentioned above is detected, and then the speed of the motor 4 is controlled so as to be within the range of negative correlation. When one operation does not provide the negative correlation, the motor 4 is driven again within the other speed range. In this manner, the motor can be controlled easily so as to be within the speed range between the t-point and the s-point, without actually detecting the t-point and the s-point. The speed of the motor 4 may be increased or decreased within the predetermined range.

The detecting timing of the t-point and the s-point or whether or not the motor speed is within the desired range as is described above may be selected suitably according to clinical conditions.

In the embodiment described above, the current measuring unit 7 is used as means for measuring flow rate by the pump 1 with the configuration in which current value provides a value corresponding to the flow rate. However, the flow rate may be directly measured with using a flow sensor. For example, an ultrasonic flow meter can be attached to the blood feeding pipe 3, and the output thereof may be processed by the amplitude detection unit 8. In this case, the amplitude detection unit 8, which is flow rate amplitude detection means, may just output the amplitude of the output fluctuation by the flow sensor, and it is not necessary to index the amplitude as in the case of using the current value of the motor 4 described above.

When an input signal from the current measuring unit 7 is digitized as is described above, a computer program can easily automates analyses, diagnoses and controls. On the other hand, when it is an analog signal, analyses, diagnoses and controls can be manually performed by visually displaying current amplitude, thereby also serving as a simple and effective method. Of course, a similar device with manual operations may be configured using digitized signals.

Figure 2B:
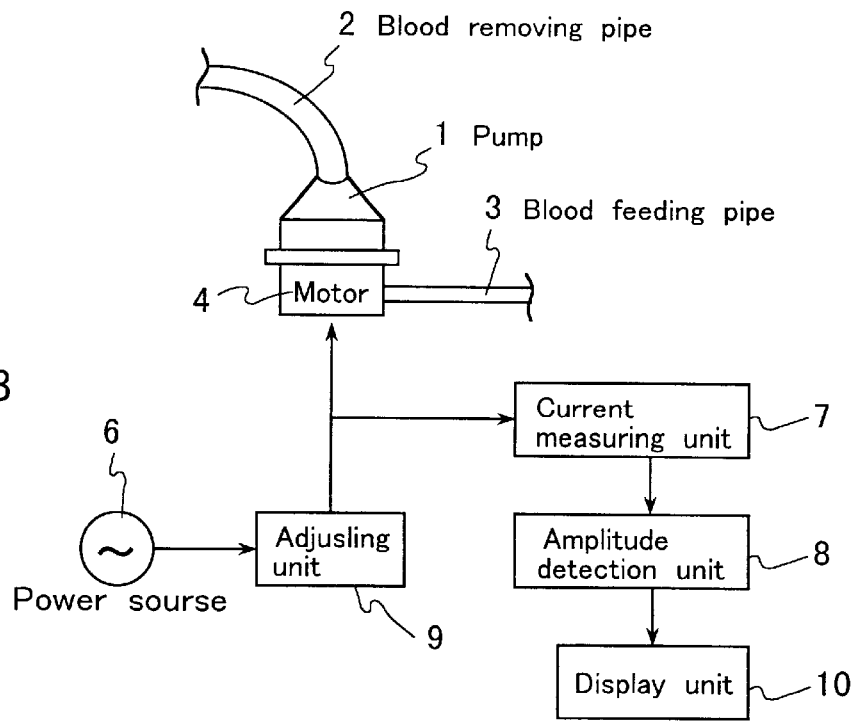
FIG. 2B is a block diagram showing a blood circulation assisting device in accordance with another embodiment of the present invention.

FIG. 2B shows an example of such a device.

In FIG. 2B, the configurations of a pump 1, a blood removing pipe 2, a blood feeding pipe 3, a motor 4, a current measuring unit 7 and an amplitude detection unit 8 are the same as the above embodiment, so the explanation here is omitted. The motor 4 is connected to a power source 6 via an adjusting unit 9. An output of the amplitude detection unit 8 is applied to a display unit 10. In other words, data indicating the detected current fluctuation amplitude is provided visually by the display unit 10. An operator can operate the adjusting unit 9 based on this data and adjust the motor 4 to an appropriate running state.

The data displayed on the displaying unit 10 may be in various forms. For example, it may be a numerical value indicating current amplitude, the maximum and minimum values of amplitude, a value of index of current amplitude, etc. Alternatively, it may be a waveform showing alteration of current amplitude or index of current amplitude.

When using the device according to the present embodiment, it is possible to display current amplitude waveform on the display unit 10 and identify the t-point or the s-point with a visual observation.

When manually conducting diagnoses and controls, it is effective to provide the device with the function of indicating that present pump drive condition is near the t-i point or the s-point. Incorporating these systems of analyses, diagnoses and controls into a motor controller can permit miniaturization and simplification of the device. On the other hand, they may be separate devices.

The device described above may be used for either a short-term assistance or a long-term assistance. Also, it may be provided externally or embedded internally in an organism.

Furthermore, by using the device according to the above embodiment, the configuration of a diagnosis device for blood circulation state in an organism is possible. For example, by using the device shown in FIG. 2B, a circulation state can be determined from the displayed content on the displaying unit 10. Also, it is more useful to further process an output of the amplitude detection unit 8 into a direct indicator for circulation state and display it on the displaying unit 10.

The following are experimental examples in animal experiments conducted in the case where the blood circulation assisting device in accordance with the present invention was attached to an organism for use in blood circulation assistance in the organism.

EXPERIMENT 1

Experiments were conducted using eight beagle dogs (weight 10.2–17.2 kg, mean 13.6 kg). Under general anesthesia due to endotracheal intubation and with controlled ventilation, the heart was exposed through a thracotomy at the left 5th intercostal space. The left atrial appendage was incised, and a blood removing pipe was inserted into the left ventricle via the mitral valve such that blood inflow site was located therein. A blood feeding pipe was used to perform end-to-side anastomosis on the thoracic descending aorta. A mixed flow pump with an impeller diameter of 32 mm was used. As for motor current consumption of the pump, aortic pressure, left ventricular pressure and pump flow rate, the waveforms were monitored. The pump speed was continuously increased from 2300 rpm to 5000 rpm. FIG. 1 shows an example of the relation between the speed and each monitoring indicator.

Since a mean value of motor current consumption increases as the speed increases, amplitude also tends to increase. Therefore, in order to show the alteration of amplitude distinctly, an index of current amplitude that was obtained by dividing the amplitude with simultaneous mean current value was used as an indicator.

In order to distinguish the points at which circulation assistance of the pump turned from partial to total based on an identification technique, the point that was identified by systolic aortic pressure and systolic left ventricular pressure was termed t-p point, and the point that was identified by the index of current amplitude was termed t-i point. As is clearly shown in FIG. 1, the index of current amplitude peaked at the t-i point and showed the minimum value at the s-point. Both the t-i point and the s-point were distinctive and easily identified.

At the speed higher than the s-point, current waveform became turbulent, which was typical of sucking, and index of current amplitude also increased again. This graph shows the speed of 2800 rpm at the t-i point and 3600 rpm at the s-point. Examining the systolic aortic pressure and the systolic left ventricular pressure, it can be seen that as the speed increased, the systolic aortic pressure and the systolic left ventricular pressure were congruent with each other up to the t-p point, but separated after the t-p point, whereafter the systolic left ventricular pressure decreased. This condition did not allow aortic valve to open, so blood was not ejected from the left ventricle to the aorta. This meant that pump changed from partial to total assistance.

This experiment showed the complete congruity in the speed at the t-p point and the t-i point. The t-i point, which was identified by the index of current amplitude, was congruent with the point at which the pump changed from partial to total assistance. The systolic left ventricular pressure lowered until the s-point, though it did not drop further at the higher speeds. Thus, the maximum stress reduction of the heart was obtained at the s-point, and the still higher speeds were dangerous because they might cause cardiac injury due to distinctive sucking. The pump flow rate increased along with the speed increase.

In the present experiment, the cardiac output was 0.92 L/min before attaching the pump. The graph in FIG. 1 shows pump blood flow rate of 1.1 L/min at the t-i point, which is substantially congruent with venous return volume. Although the pump blood flow rate increased from the t-i point to the s-point, the aortic pressure did not increase. This seems to reflect the ineffective blood flow increase such as reversed flow at aortic valve, rather than the effective blood flow increase to an organism. At the speed higher than the s-point, pump blood flow rate did not increase due to distinctive sucking.

In order to identify the t-point and the s-point, the pump speed is changed actively, and a computer automatically calculates the relationship between the speed and index of current amplitude. The changing operation of the speed may be performed constantly, intermittently or in the case where some kind of disorder is detected.

The present experiment identified the t-point or the s-point by measuring systolic left ventricular pressure, index of current amplitude etc., within the pump speed variation range of 2000–5000 rpm. However, in the clinical setting, it is not always necessary for the pump speed variation range to be large as is described above. For example, when the variation range is set at approximately 100 rpm, and a negative correlation between the speed and the index of current amplitude is seen, it can be concluded that the pump is driven between the t-point and the s-point. Therefore, it is preferable that the pump speed is controlled to be near the t-point or the s-point (including each point), or between the t-point and the s-point including the vicinity of the t-point and the s-point.

EXPERIMENT 2

Eight beagle dogs underwent a formation of cardiac insufficiency due to a temporary obstruction of coronary artery and an infusion load test. The three branches of the anterior descending coronary artery, that were central, peripheral and main branches of the circumflex artery (usually obtuse marginal branch), were occuluded for 30 minutes and then released. After releasing, pump support was carried out for 120 minutes. Finally, 500 ml of low molecular weight dextran was rapidly infused to apply load. The identification test of the t-point and the s-point was conducted by continuously changing the speed seven times temporarily, which were before coronary obstruction, during obstruction, 30, 60, 90 and 120 minutes after the obstruction, and post-infusion. The results from a total of 52 identification tests of measuring the t-points and the s-points were processed statistically.

Figure 3:
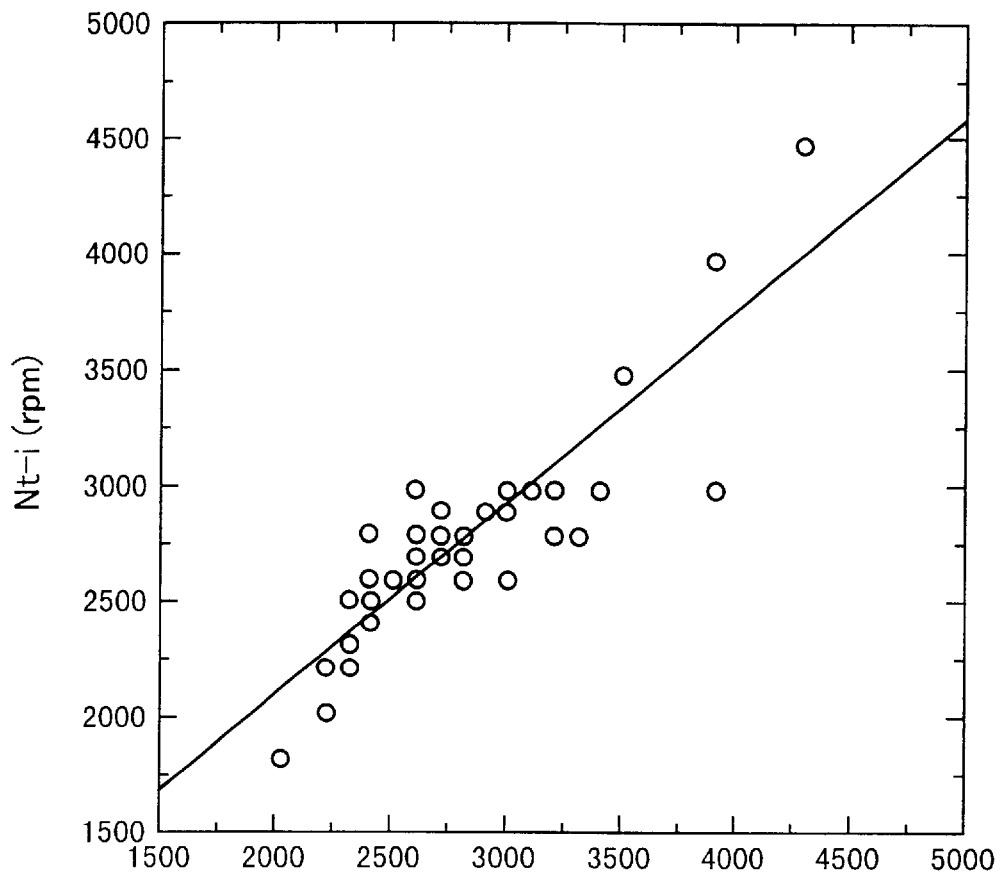
FIG. 3 is a diagram showing the relationship between pump speeds at the t-p point and the t-i point.

In terms of the relationship between the t-p point that was identified by systolic aortic pressure and systolic left ventricular pressure and the t-i point that was identified by index of current amplitude, the speeds at both points (Nt-p and Nt-i) highly correlated with each other (multiple correlation coefficient $R^2=0.787$), and significant regression coefficient was obtained (significance level $P<0.0001$) (FIG. 3). The result indicated that the pump assistance state could be diagnosed with current amplitude.

In order to examine the significance in pump control at the t-point, a multiple regression analysis was conducted by setting the pump flow rate at the t-i point (Qt-i) as objective variable and the left ventricular pressure dp/dt measured by momentarily occluding the pump (dp/dt), the left ventricular end diastolic pressure (LVEDP) and the systolic aortic pressure (AoPsys) as explanatory variables, resulting in a high correlation (multiple correlation coefficient $R^2=0.559$). In each regression coefficient test, only LVEDP was significant (dp/dt: $P=0.21$, LVEDP: $P<0.0001$, AoPsys: $P=0.37$).

dp/dt described above, which was obtained by differentiating pressure change with time, shows pressure change over time and serves as an indicator for a systolic power in a clinical setting.

Figure 4:
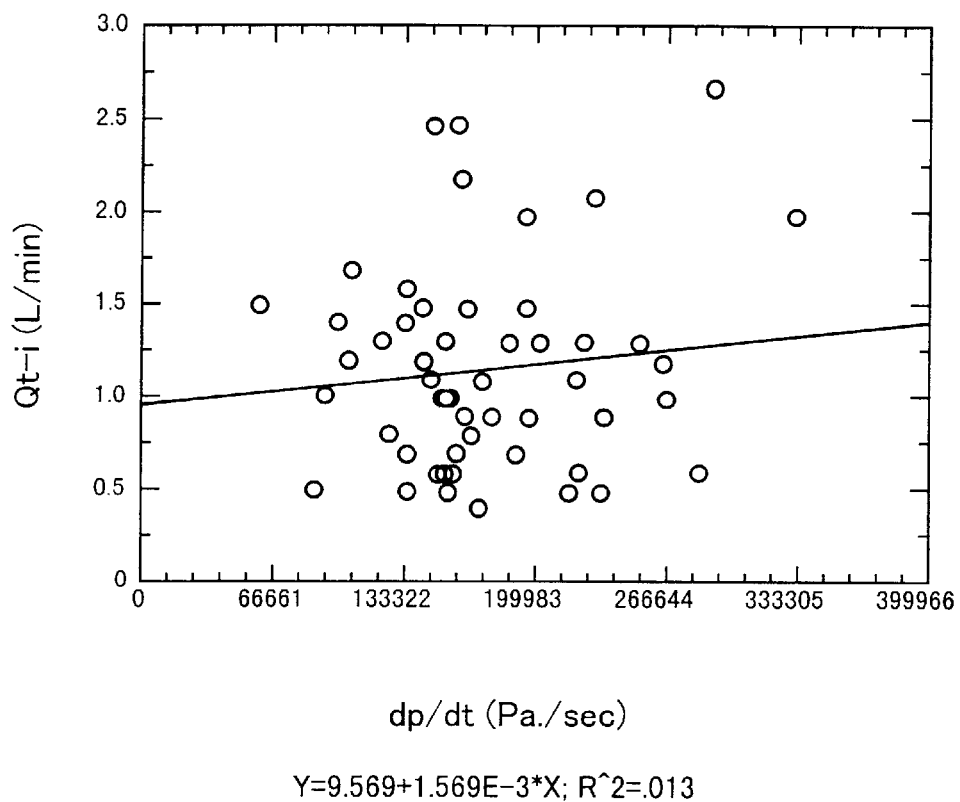
FIG. 4 is a diagram showing the relationship between pump flow rate at the t-i point and left ventricular dp/dt.
Figure 5:
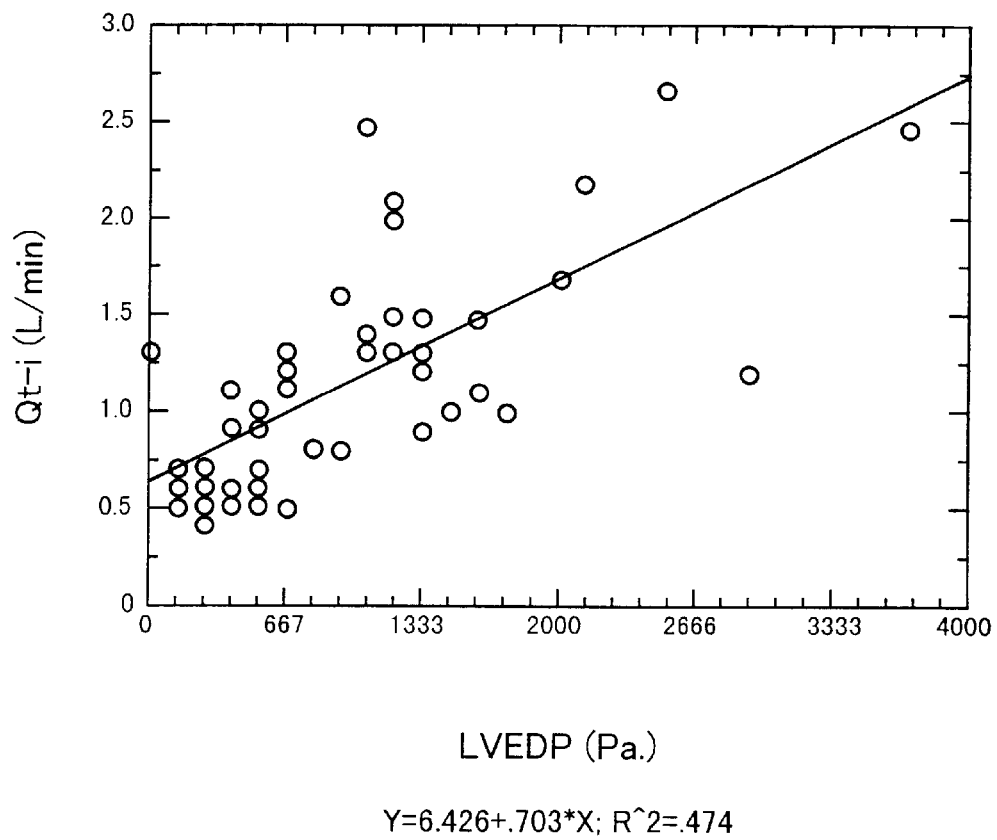
FIG. 5 is a diagram showing the relationship between pump flow rate at the t-i point and left ventricular end diastolic pressure.
Figure 6:
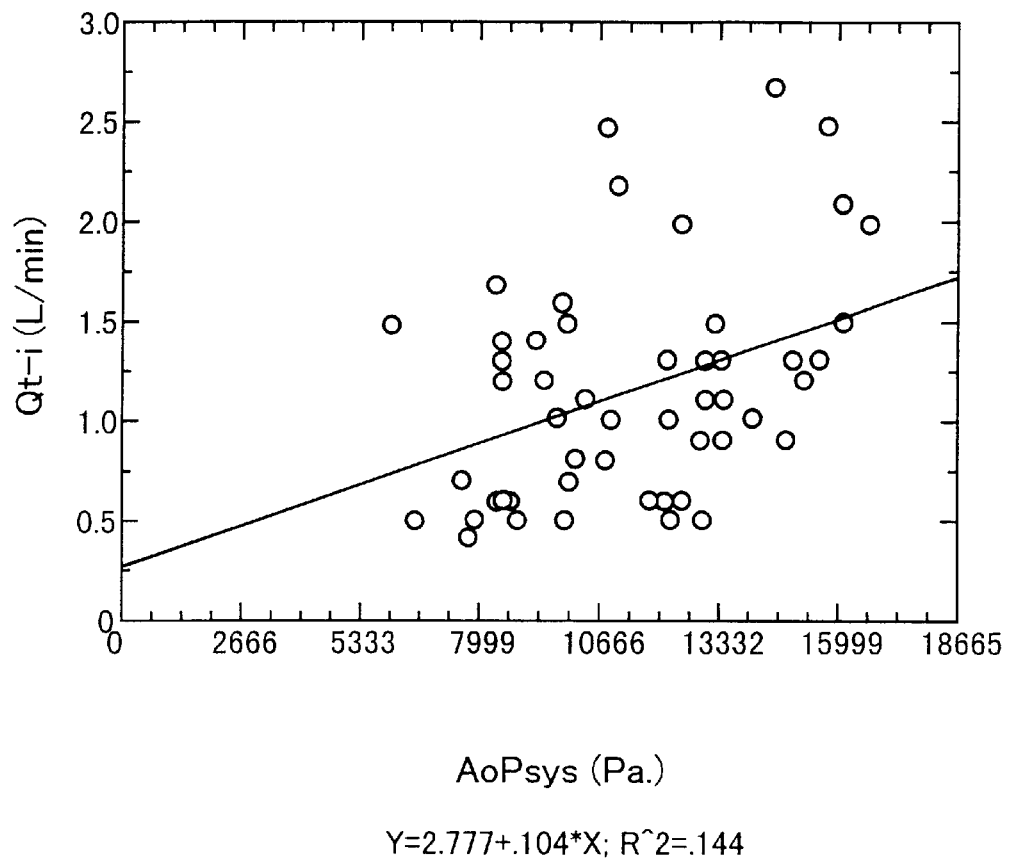
FIG. 6 is a diagram showing the relation between pump flow rate at the t-i point and systolic aortic pressure.

Each single correlation coefficient was $R^2=0.013$ between pump flow rate at the t-i point and left ventricular dp/dt (FIG. 4), $R^2=0.474$ between pump flow rate at the t-i point and LVEDP (FIG. 5), and $R^2=0.144$ between pump flow rate at the t-i point and systolic aortic pressure (AoPsys) (FIG. 6).

The results showed the pump flow rate at the t-i point and the left ventricular end diastolic pressure (LVEDP) highly correlated with each other. In other words, it was considered that the pump flow rate at the t-i point was determined by left ventricular preload (indicates blood volume returning to the heart) and not dependent on left ventricular contractility and afterload. This was reasonable and efficient in that blood volume present in the heart was sent out, and close to the control by a natural heart or a pulsatile artificial heart.

INDUSTRIAL APPLICABILITY

According to the present invention, a continuous flow blood pump can be controlled in an optimal state matching a blood circulation state in an organism. The device with a simple structure achieves an optimal blood circulation assistance without any specific sensor. In addition to this, the present invention easily can diagnose the circulation state in the organism.

As is described above, the present invention realizes the blood circulation assisting device or the diagnosis device for circulation state with simple structure and excellent functions.

What is claimed is:

1. A blood circulation assisting device comprising:
   a continuous flow blood pump comprising a non-displacement-type pump for blood feeding assistance,
   a motor for driving said continuous flow blood pump,
   a blood removing pipe having one end attachable to a blood removal site in an organism and the other end connected to an inflow portion of said continuous flow blood pump,
   a blood feeding pipe having one end attachable to a blood feed site in the organism and the other end connected to an outflow portion of said continuous flow blood pump,
   wherein blood is removable via said blood removing pipe and drivable out via said blood feeding pipe by said continuous flow blood pump so as to attain a predetermined flow rate,
   said blood circulation assisting device further comprising flow rate detection means for directly or indirectly obtaining data corresponding to a blood flow rate flowing through said continuous flow blood pump,
   fluctuation amplitude detection means for obtaining, from an output of said flow rate detection means, data corresponding to a fluctuation amplitude of the flow rate,
   specific point detection means for detecting at least one of a t-point and a s-point, the t-point and the s-point being a starting point and an end point, respectively of a range where the fluctuation amplitude of the flow rate shows a negative correlation with a speed of the motor, and
   adjusting means for adjusting a motor speed based on an output of said specific point detection means.

2. The blood circulation device according to claim 1, wherein said flow rate detection means is configured so that an output corresponding to the flow rate is obtainable by measuring a current consumption or a power consumption value of the motor.

3. The blood circulation assisting device according to claim 2, wherein said fluctuation amplitude detection means detects a mean output and an output fluctuation amplitude of said flow rate detection means at predetermined time intervals and outputs an amplitude index that is obtained by dividing the fluctuation amplitude with the mean output.

4. The blood circulation assisting device according to claim 3, wherein said adjusting means comprises control means for controlling the motor speed according to the output of said fluctuation amplitude detection means so that the amplitude index is within a predetermined range.

5. The blood circulation assisting device according to claim 2, wherein said specific point detection means is capable of detecting the t-point and the s-point, and the control means controls the motor speed so as to correspond to the speed between near the t-point and near the s-point.

6. The blood circulation assisting device according to claim 1, wherein said flow rate detection means is configured so that an output corresponding to the flow rate is obtained by using a flow sensor disposed near said continuous flow blood pump.

7. The blood circulation assisting device according to claim 1, wherein said fluctuation amplitude detection means detects a maximum value and a minimum value of the output of said flow rate detection means at predetermined time intervals and outputs the maximum value and the minimum value.

8. The blood circulation assisting device according to claim 1, wherein said fluctuation amplitude detection means outputs the fluctuation amplitude that is a difference between a maximum value and a minimum value of the output of said flow rate detection means.

9. The blood circulation assisting device according to claim 8, wherein said adjusting means comprises control means for controlling the motor speed according to the output of said fluctuation amplitude detection means so that the amplitude is within a predetermined range.

10. The blood circulation assisting device according to claim 9, wherein said control means is capable of identifying the t-point or s-point by forcing the motor to change its speed temporarily so as to cause the fluctuation amplitude to vary and detecting the correlation between the fluctuation amplitude of the flow rate and the speed of the motor based on the change of the fluctuation amplitude.

11. The blood circulation assisting device according to claim 1, wherein said specific point detection means comprises display means for displaying the output of said fluctuation amplitude detection means, and said adjusting means comprises means for manually operating and adjusting a speed of the motor driving said pump.

12. The blood circulation assisting device according to claim 1, wherein said adjusting means comprises control means for controlling automatically motor speed so as to be in a predetermined relation to the motor speed at the detected t-point and/or s-point.

13. The blood circulation assisting device according to claim 12, wherein said control means controls the motor so as to have a speed corresponding to the t-point or near the t-point.

14. The blood circulation assisting device according to claim 12, wherein said control means controls the motor so as to have speed corresponding to the s-point or near the s-point.

15. A diagnosis device for blood circulation state comprising said blood circulation assisting device according to claim 1, wherein, when said device is attached to an organism, the speed of the motor is changed, a t-point at which circulation assistance by said pump changes from partial to total assistance is detected based on an output change of said flow rate amplitude detection means caused by the change of the motor speed, and an inflow state at a blood inflow port and/or filling state of a heart are detected based on the flow rate amplitude at the detected t-point or near the t-point.

16. A methyl for diagnosing an organism, wherein the device according to claim 15 is attached to the organism to diagnose a blood circulation state.

17. A diagnosis device for blood circulation state comprising said blood circulation assisting device according to claim 1, wherein, when said device is attached to an organism, the speed of the motor of said continuous flow blood pump is changed, a t-point at which circulation assistance by said pump changes from partial to total assistance is detected based on an output change of said flow rate amplitude detection means caused by the change of the motor speed, the speed change of the motor corresponding to the detected t-point or near the t-point is detected, and a change of circulation state in the organism is detected with the speed change.

18. The diagnosis device for blood circulation state according to claim 17, wherein, when the speed of the motor corresponding to the t-point or near the t-point increases, unchanged blood pressure is judged as an increase of venous return or unchanged venous return is judged as an increase of blood pressure.

19. The diagnosis device for blood circulation state according to claim 17, wherein, when the speed of the motor corresponding to the t-point or near the t-point decreases, unchanged blood pressure is judged as an increase of venous return decrease or unchanged venous return is judged as an increase of blood pressure.

20. The diagnosis device for blood circulation state comprising said blood circulation assisting device according to claim 1, wherein, when said device is attached to an organism, the speed of the motor is changed, an s-point at which a fluctuation of the flow rate amplitude becomes distinctive because a blood inflow port of said blood removing pipe starts sucking on to a wall of the organism is detected based on an output change of said flow rate amplitude detection means caused by the change of the motor speed, and an inflow state at the blood inflow port and/or filling state of a heart are detected based on the flow rate amplitude at the detected s-point or near the s-point.

21. The diagnosis device for blood circulation state comprising said blood circulation assisting device according to claim 1, wherein, when said device is attached to an organism, the speed of the motor is changed, an s-point at which a fluctuation of the flow rate amplitude becomes distinctive because a blood inflow port of said blood removing pipe starts sucking on to a wall of the organism is detected based on an output change of said flow rate amplitude detection means caused by the change of the motor speed, the speed at the detected s-point or near the s-point is detected, and a change of circulation state in the organism is diagnosed with the speed change.

22. A method of assisting blood circulation in an organism, wherein the device according to claim 1 is attached to the organism to assist blood circulation.

* * * * *